United States Patent [19]

Nakamura et al.

[11] Patent Number: 5,160,604
[45] Date of Patent: Nov. 3, 1992

[54] TOXIC SUBSTANCE-DETECTING SYSTEM WITH FIXED MICROORGANISM MEMBRANE FOR WATER QUALITY-MONITORING

[75] Inventors: Eiichi Nakamura; Hiroaki Tanaka, both of Ibaraki; Yoshiharu Tanaka, Kanagawa; Takashi Iitake, Kanagawa; Hiroshi Hoshikawa, Kanagawa, all of Japan

[73] Assignees: Fuji Electric Co., Ltd., Kanagawa; Public Works Research Institute, Ibaraki, both of Japan

[21] Appl. No.: 649,863

[22] Filed: Feb. 5, 1991

[30] Foreign Application Priority Data

Feb. 5, 1990 [JP] Japan .................................. 2-25654
Dec. 26, 1990 [JP] Japan ................................. 2-406437

[51] Int. Cl.$^5$ ............................................ C12M 1/34
[52] U.S. Cl. .................................... 210/85; 73/863.24; 204/153.12; 204/153.16; 210/96.2; 210/321.69; 210/500.29; 364/497; 422/79; 435/32; 435/252; 435/260; 435/289; 435/291; 435/316
[58] Field of Search .................. 204/153.12, 153.16; 73/863.01, 863.21, 863.23, 863.24; 210/85, 92, 96.1, 96.2, 102, 103, 143, 259, 418, 436, 472, 500.27, 500.29, 500.36, 63.7; 435/3, 4, 29, 32, 288, 289, 291, 311, 807, 817; 422/67, 79, 110, 111; 364/497, 502; 116/209

[56] References Cited

U.S. PATENT DOCUMENTS

| | | | |
|---|---|---|---|
| 3,981,777 | 9/1976 | Alsop | 435/32 |
| 4,162,195 | 7/1979 | Solymon et al. | 210/96.1 |
| 4,260,490 | 4/1981 | Moss et al. | 210/96.1 |
| 4,297,173 | 10/1981 | Hikuma et al. | 435/288 |
| 4,564,453 | 1/1986 | Coplot et al. | 435/32 |
| 4,573,354 | 3/1986 | Vorhees et al. | 73/863.21 |
| 4,620,930 | 11/1986 | McDowell | 435/32 |
| 4,748,127 | 5/1988 | Siepmann et al. | 435/32 |
| 4,783,750 | 11/1988 | Smith | 364/497 |
| 5,106,511 | 4/1992 | Kodukuca | 210/143 |

FOREIGN PATENT DOCUMENTS

| | | |
|---|---|---|
| 2513650 | 10/1976 | Fed. Rep. of Germany ........ 435/32 |
| 2651896 | 5/1978 | Fed. Rep. of Germany ........ 435/32 |
| 2189605 | 10/1987 | United Kingdom .................. 435/32 |

OTHER PUBLICATIONS

Rawson et al., "Whole-Cell Biosensors for Environmental Monitoring," Biosensors, 1989, pp. 299-311.
Kashiwagi et al., "A System to Enhance Surveillance of Water Quality in an Area Containing Soiled Water by Means of Fish that Have Artificial Intelligence", Environmental Technology, 1988.
Katsuura et al., "A Water Quality Surveillance Device that Centers On the Amount Fish Breathe", Environmental Technology, 1988.

*Primary Examiner*—Mary Lynn Theisen
*Assistant Examiner*—Joseph Drodge
*Attorney, Agent, or Firm*—Finnegan, Henderson, Farabow, Garrett and Dunner

[57] ABSTRACT

A toxic substance-detecting device detects toxic substances in water by use of a microorganism sensor to ascertain the safety of affluents flowing into sewage-treating processes, environmental waters such as rivers, and waters flowing into water purification plants and a water quality-monitoring system employing a detecting device. The device includes a fixed micro-organism membrane and apparatus for circulating a buffer solution of micro-organism substrate and nutrient to one side of the membranne and solutions of water to be examined, standard and cleaning water to the other side.

22 Claims, 7 Drawing Sheets

TOXIC SUBSTANCE-DETECTING SYSTEM WITH FIXED MICROORGANISM MEMBRANE FOR WATER QUALITY-MONITORING

BACKGROUND OF THE INVENTION

1. Field of the Invention

The present invention relates to a toxic substance-detecting device which detects toxic substances in water by use of a microorganism sensor to ascertain the safety of affluents flowing into sewage-treating processes, environmental waters such as rivers, and waters flowing into water purification plants. The present invention also relates to a water quality-monitoring system employing a detecting device.

2. Discussion of the Related Art

If toxic substances, such as phenols, cyanogen, arsenic, and heavy metals, accidentally come into contact with wastewaters discharged from factories and the contaminated wastewaters flow into sewage works, the activated-sludge microorganisms (hereinafter referred to as activated sludges) which play a major role in the sewage-treating processes can be severely damaged.

High concentrations of such toxic substances lower the activity of the activated sludges which greatly increases recovery time. If the inflow of wastewater contaminated by a toxic substance can be detected beforehand, water contamination from toxic substances can be greatly diminished by conducting a neutralization treatment in the primary sedimentation tank before the activated sludge treatment. For this reason, a device is desired that can detect the presence of a toxic substance in wastewater before the inflow of wastewater or at the time the wastewater has just flowed into sewage works.

Although the discharge of toxic substances may be controlled by regulating the concentrations of specific chemical substances in wastewaters, measuring techniques which have been developed heretofore cannot determine the concentrations of all toxic substances and are insufficient in maintaining the quality of all public waters. To measure the concentrations of toxic substances, there are techniques such as colorimetry and ion electrode method for cyanogen, atomic-absorption spectroscopy for heavy metals and GC-MS method for agricultural chemicals. However, it is technically and economically difficult to conduct continuous chemical examinations for determining the concentrations of a variety of toxic substances.

In the case of tap water, however, there has been proposed a method to control the quality of inflowing waters by means of a biological toxicity test. In this method, 10 to 20 fish are released in a pool filled with the water to be examined and the presence or absence of a toxic substance or the degree of toxicity is judged from the reactions and death rate of the fish after a fixed time period. However, this method, in which the water quality is judged based on the behavior and health condition of each fish, is defective in that the method is ambiguous and not suited for quantitative analysis, and factors which may affect the behavior of the fish is not taken into account. Therefore, the success of this method greatly depends on the experience of the operator and detection of toxic substances in early stages is difficult.

The conventional methods described above have the following practical problems: (1) clear results require a long period of time which prevents prompt treatment of the contamination; and (2) only high levels of concentration are detectable, i.e. toxic substances present at low concentrations cannot be detected.

SUMMARY OF THE INVENTION

The present invention has been made in view of the above circumstances and has an object of providing a toxic substance-detecting device which can speedily and readily detect toxic substances in water. The toxic substances to be detected in the present invention are those defined as a toxic substance or a lethal substance in laws such as *Water Quality Pollution Prevention Law* (Environment Standard and Draining Standard), *Water Supply Law* (Water Quality Standard) and *Toxic Substance and Lethal Substance Control Law*. These substances are also illustrated, for example, in *Method for Examining Service Water* (Determination of Toxic Substance in Water, pp. 730-753, ed. by Ministry of Public Welfare, published by Japan Association of Water Supply, 1985).

Another object of the present invention is to provide a water quality-monitoring system employing the above detecting device.

These and other objects are attained by a toxic substance-detecting device including a microorganism sensor having a combination of a flow cell and a dissolved oxygen electrode, a circulating system which circulates a buffer solution and sends the buffer solution to one side of a fixed-microorganism membrane, a flow control system which selectively sends water to be examined, a standard solution for calibrating the microorganism sensor, or a cleaning water to be sent to another side of said fixed-microorganism membrane, and an arithmetic and control circuit which processes output signals from the microorganism sensor and controls an operation of the toxic substance-detecting device.

According to another aspect, the present invention includes a water quality-monitoring system having a microorganism sensor having a combination of a flow cell and a dissolved oxygen electrode, a circulating system which circulates a buffer solution and sends the buffer solution to one side of a fixed-microorganism membrane, a flow control system which selectively sends water to be examined, a standard solution for calibrating said microorganism sensor, or a cleaning water to be sent to another side of the fixed-microorganism membrane, an arithmetic and control circuit which processes output signals from the microorganism sensor and controls the operation of a toxic substance-detecting device, a water-sampling device which receives output signals from the toxic substance-detecting device and continuously takes water samples to be examined, a chemical analyzer which quantitatively analyzes the water samples taken by the water-sampling device, and a toxic substance-discharging area-judging device which receives signals from the chemical analyzer and estimates the source of a toxic substance.

BRIEF DESCRIPTION OF THE DRAWINGS

The manner by which the above objects and other objects, features, and advantages of the present invention are attained will be fully apparent from the following detailed description when it is considered in view of the drawings, wherein.

DESCRIPTION OF THE PREFERRED EMBODIMENTS

Figure 1A:
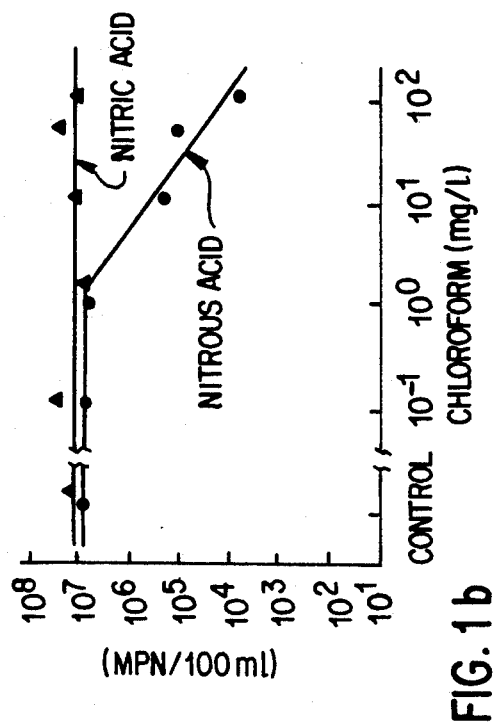
FIGS. 1 (a) to (d) are graphic representations showing the relationships between toxic substance concentration and the most probable number of the microorganism (MPN) for a nitrous acid-producing bacteria or a nitric acid-producing bacteria.
Figure 1C:
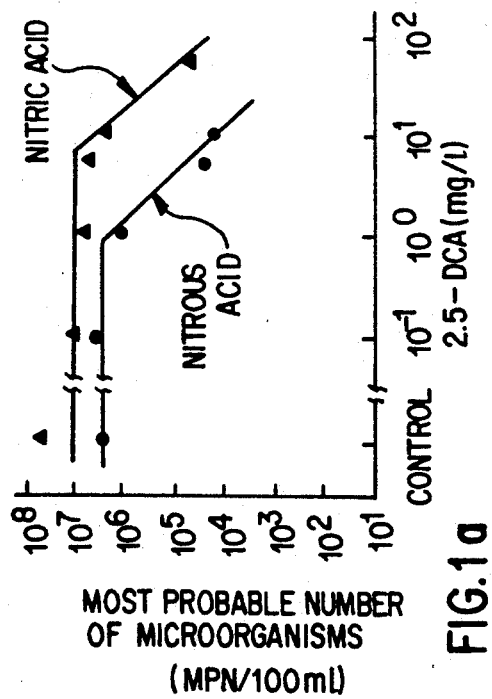
Figure 1B:
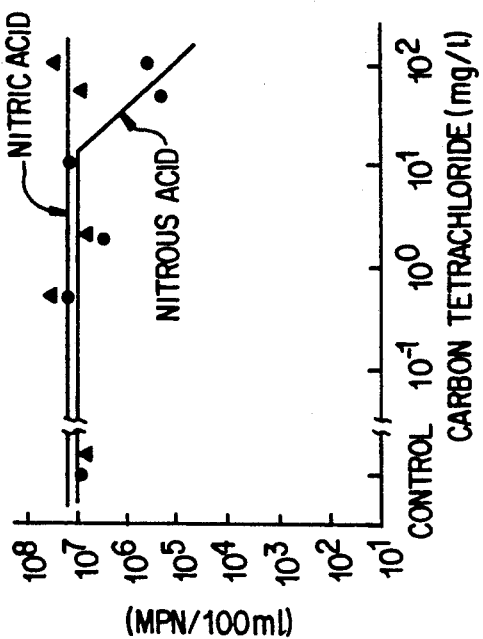
Figure 1D:
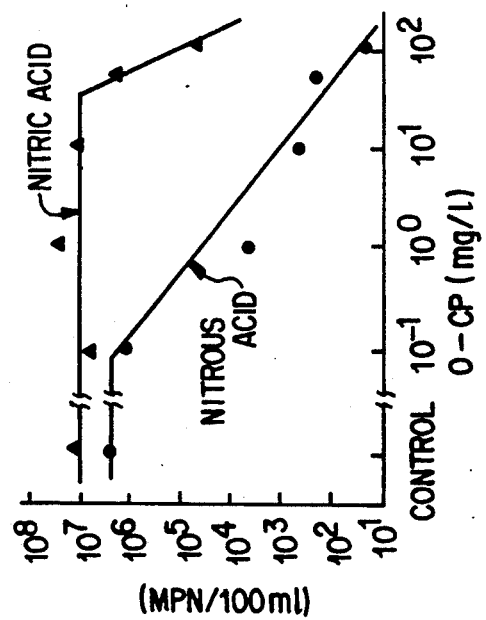

The toxic substance-detecting device of the present invention, which eliminates the conventional problems described above, includes a microorganism sensor including a combination of a flow cell and a dissolved oxygen electrode in which the flow cell includes a fixed-microorganism membrane on which nitrous acid-producing bacteria have been fixed and two flow channels in contact with both sides of the fixed-microorganism membrane, respectively. The dissolved oxygen electrode is in contact with one side of the fixed-microorganism membrane through a gas-permeable membrane.

A circulating system circulates a buffer solution and sends the buffer solution to one side of the fixed-microorganism membrane where the buffer solution contains a predetermined concentration of ammonia nitrogen that is a substrate for the nitrous acid-producing bacteria. The nitrous acid-producing bacteria as used in the present invention means the bacteria capable of aerobically oxidizing ammonia to produce nitrous acid which are sensitive toxic substances to be detected by the toxic substance-detecting device of the present invention, including the bacteria belonging to the genera of Nitrosomonas, Nitrosospira, Nitrosococcus, Nitrosolobus, Nitrosocystis and Nitrosogloea. A flow control system selectively sends water to be examined, a standard solution for calibrating the microorganism sensor or cleaning water to be sent to the other side of the fixed-microorganism membrane, where the water to be examined and the standard solution are saturated with dissolved oxygen before being sent to the other side of the fixed-microorganism membrane. An arithmetic and control circuit processes output signals from the microorganism sensor and controls the operation of the toxic substance-detecting device.

In another aspect of the present invention, a water quality-monitoring system employs the above-described toxic substance-detecting device and includes a water-sampling device connected to the toxic substance-detecting device for receiving output signals from the toxic substance-detecting device and for continuously taking water samples to be examined. A chemical analyzer quantitatively analyzes the water samples taken by the water-sampling device. A toxic substance-discharging area-judging device receives signals from the chemical analyzer and estimates the source of a toxic substance.

The toxic substance-detecting device of this invention employs a microorganism sensor which includes a combination of (1) a fixed-microorganism membrane on which a nitrous acid-producing bacteria - an autotrophic bacteria, has been fixed and (2) a dissolved oxygen electrode. To obtain a stable sensor output, a buffer solution, in an ammonia nitrogen that is a substrate for the nitrous acid-producing bacteria and a minor nutrient incorporated at predetermined concentrations, is fed to the microorganism sensor. The constant sensor output thus regulated by the feeding of such a buffer solution is caused to fluctuate if a toxic substance has come into the test water being examined or if toxic conditions such as toxic substance concentration and toxicity level are changed, and such a fluctuation of the microorganism sensor output is detected. Thus, the toxic substance-detecting device can judge whether a toxic substance is present in the test water. Further, the water quality-monitoring system employing this toxic substance-detecting device can specify the toxic substance present in the test water being examined and estimate the source of the toxic substance by driving a water-sampling device according to the output signals from the toxic substance-detecting device and continuously taking samples of the water while operating an analyzer that analyzes the water samples by chemical means.

In the beginning of the studies that have to this invention, the present inventors investigated various kinds of microorganisms. Among these, a nitrous acid-producing bacteria and a nitric acid-producing bacteria were examined for their sensitivity to toxic substances by a "drug sensitivity test." The nitrous acid-producing bacteria used was Nitrosomonas europaea which has been deposited to the American Type Culture Collection under the deposit number ATCC 25978 and the nitric acid-producing bacteria used was Nitrobactor winogradskyi. In this test, a tenfold dilution series of a toxic substance was prepared by using bouillon culture media and the bacteria to be tested was inoculated onto the culture media and cultured for a fixed period of time. Then the minimum concentration of toxic substance resulting in bacteria growth inhibition was determined. This concentration value is referred as minimum (growth) inhibitory concentration, MIC. The lower the MIC, the higher the sensitivity of the bacteria to the toxic substance, and the higher the MIC, the lower the sensitivity. The maximum concentration of toxic substance resulting in bacteria growth almost equal to that in a control culture medium containing no toxic substance is referred as maximum (growth) allowance concentration, MAC. Therefore, MAC is a lower toxic substance concentration than MIC.

The toxicity of each toxic organic chlorine compound, i.e., 2,5-dichloroaniline (2,5-DCA), chloroform, o-chlorophenol (O-CP) and carbon tetrachloride was determined with respect to a nitrous acid-producing bacteria and a nitric acid-producing bacteria. The results obtained are shown in graphs (a), (b), (c) and (d) in FIG. 1, in which the concentration (mg/l) of each toxic compound is the abscissa and the most probable number (of the microorganism), MPN, is the ordinate. MIC and MAC range values obtained from the above results are as shown in Table 1

TABLE 1

| Toxic substance | Nitrous acid-producing bacteria (mg/l) | Nitric acid-producing bacteria (mg/l) |
| --- | --- | --- |
| 2,5-DCA | 1–10 | 10–100 |
| O—CP | 0.1–1 | 10–100 |
| Chloroform | 1–10 | 100< |
| Carbon tetrachloride | 10–100 | 100< |

From these experimental results, it can be seen that the nitrous acid-producing bacteria had a higher sensitivity to all the toxic substances than the nitric acid-producing bacteria. Thus, it was concluded that the use of a nitrous acid-producing bacteria was better suited to detect certain toxic chlorine substances and based on this, the toxic substance-detecting device of this invention has been constructed.

It should be readily apparent, however, to one of ordinary skill in the art that other nitrous acid-producing bacteria might also be suitable for use in this device depending on the nature of the toxic wastes to be detected.

Figure 2:
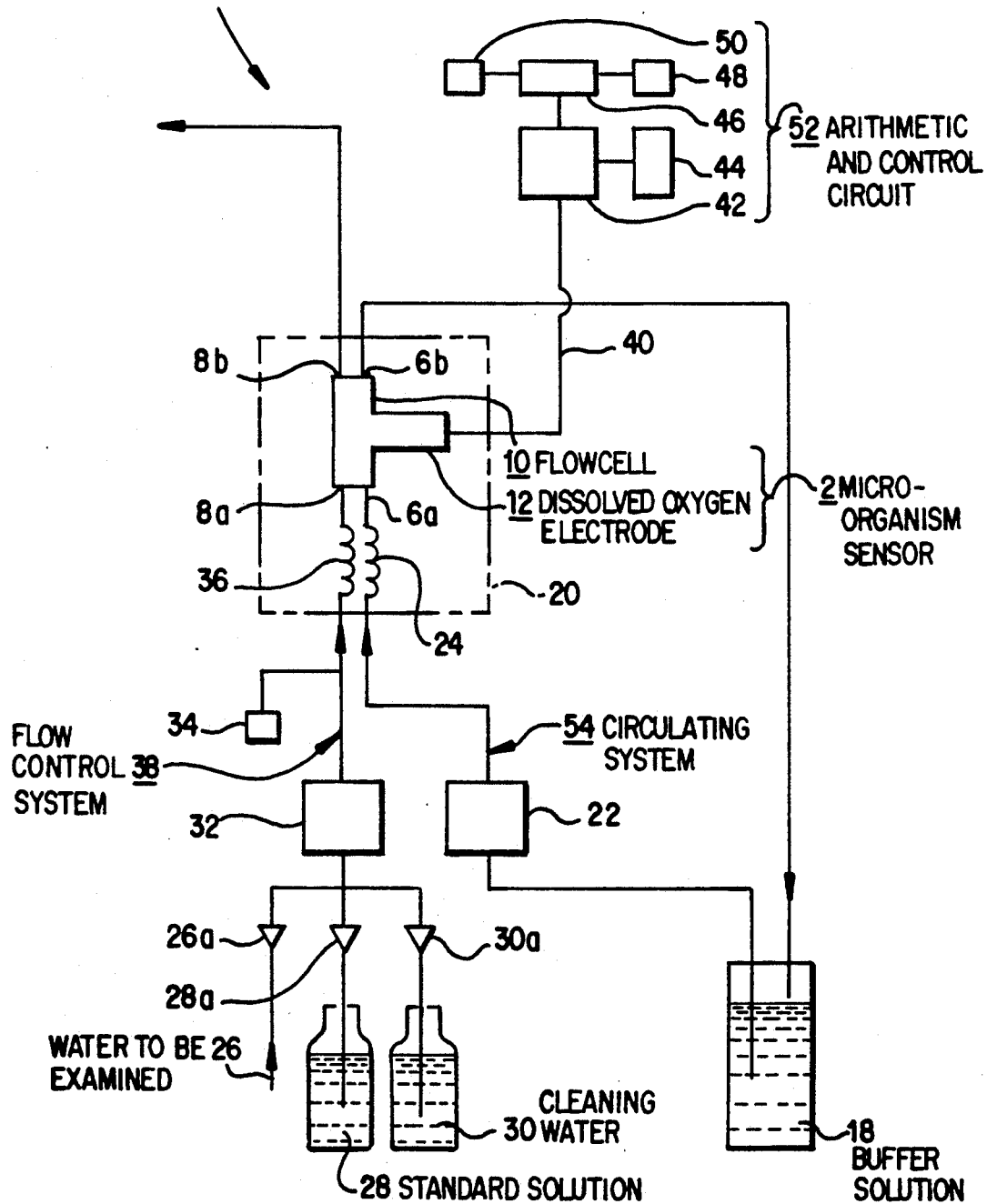
FIG. 2 is a diagrammatic view showing the construction of one embodiment of the toxic substance-detecting device of this invention and the water channels in the detecting device.

The toxic substance-detecting device of the present invention is explained below with reference to both FIGS. 2 and 3. FIG. 2 is a diagrammatic view showing the construction of the toxic substance-detecting device of this invention and FIG. 3 is a sectional view of a microorganism sensor incorporated into the toxic substance-detecting device of FIG. 2.

Figure 3:
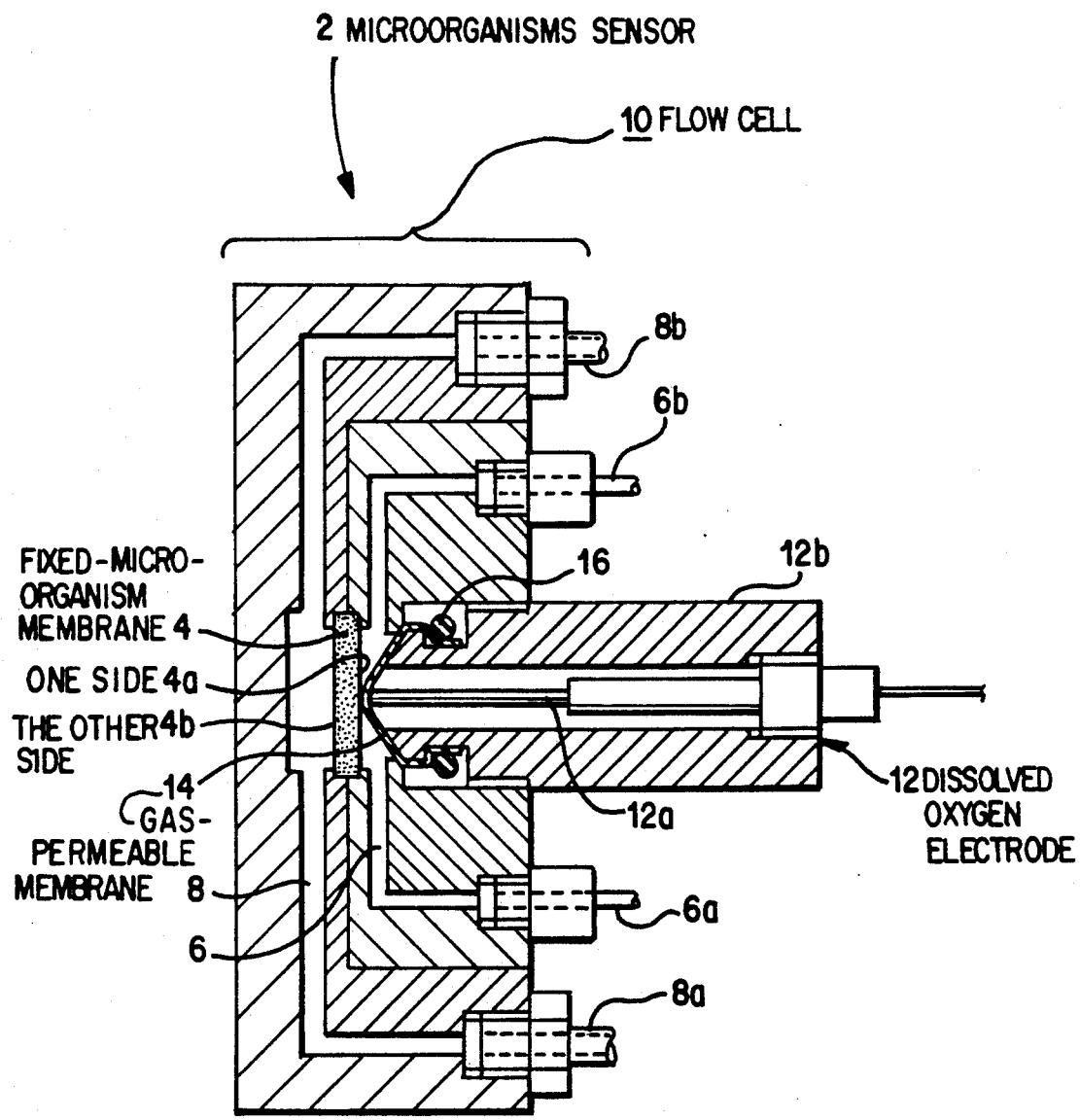
FIG. 3 is a diagrammatic sectional view of a microorganism sensor incorporated into the toxic substance-detecting device of this invention.

The microorganism sensor 2 shown in FIGS. 2 and 3 has a construction in which a flow cell 10 includes a fixed-microorganism membrane 4 obtained by fixing a nitrous acid-producing bacteria on a porous membrane and two flow channels 6 and 8 in contact with one side 4a and the other side 4b, respectively, of the fixed-microorganism membrane 4. The flow cell 10 is combined with a dissolved oxygen electrode 12 to determine the amount of dissolved oxygen in the test water. In the flow cell 10, the flow channel 6 has a buffer solution inlet 6a and a buffer solution outlet 6b, while the flow channel 8 has a test water inlet 8a and a test water outlet 8b. The dissolved oxygen electrode 12 has been arranged such that its platinum cathode 12a is in contact with one side 4a of the fixed-microorganism membrane 4 through a gas-permeable membrane 14 made of a fluoroplastic. The gas-permeable membrane 14 is fixed to the main body 12b of the dissolved oxygen electrode 12 through an O-ring 16.

The toxic substance-detecting device 1 shown in FIG. 2, according to the present invention, has a circulating system 54 which sends a buffer solution 18 containing a predetermined concentration of ammonia nitrogen that is a substrate for the nitrous acid-producing bacteria, to one side 4a of the fixed-microorganism membrane 4 in the microorganism sensor 2 by means of a pump 22. The pump 22 circulates the buffer solution from the fixed-microorganism membrane 4 through a heat exchanger 24 in the constant temperature bath 20 and through the buffer solution inlet 6a, flow channel 6, and buffer solution outlet 6b in the flow cell 10. The microorganism sensor 2 is installed in a constant temperature bath 20 shown by a dotted line in FIG. 2. The toxic substance-detecting device of this invention also has a flow control system 38 which selectively sends, by means of a pump 32, a test water 26 for examination, a standard solution 28 for calibrating the microorganism sensor 2, or a cleaning water 30 by opening or closing respective valves 26a, 28a, and 30a through a heat exchanger 36 in the constant temperature bath 20 through the test water inlet 8a, flow channel 8 and test water outlet 8b in the flow cell 10 to the other side 4b of the fixed-microorganism membrane 4.

Test water 26 and standard solution 28 are saturated with dissolved oxygen by means of an air pump 34 before being sent as described above. Output signals from the dissolved oxygen electrode 12 in the microorganism sensor 2 pass through a signal wire 40 to an arithmetic and control circuit 52 including an instrumentation unit 42, a control unit 44, an arithmetic unit 46, a display 48, and a recorder 50. In this arithmetic and control circuit, the output signals are processed and the results of the detection by the microorganism sensor 2 are displayed and recorded based on which operation of the toxic substance-detecting device 1 is controlled.

The toxic substance-detecting device 1 is further explained below with respect to its operation. First, calibration of the microorganism sensor 2 is conducted using the standard solution 28 while the circulating system 54 is being operated to circulate the buffer solution 18. This buffer solution 18 is a solution prepared by adding a nutrient for the nitrous acid-producing bacteria such as calcium chloride (CaCl$_2$) and magnesium sulfate (MgSO$_4$) added to a phosphoric acid buffer solution having a pH of 8.0 and by further incorporating thereinto, at a concentration of 2.0 mg/l, an ammonia nitrogen that is a substrate for the nitrous acid-producing bacteria. The standard solution 28 is a solution containing o-chlorophenol (O-CP) at a fixed concentration.

Upon operation of the circulating system 54 by means of the pump 22, the buffer solution 18 is heated to about 30° C. by the heat exchanger 24 in the constant temperature bath 20, subsequently brought into contact with one side 4a of the fixed-microorganism membrane 4 in the microorganism sensor 2, and then discharged. The discharged buffer solution is circulated again in the same way as above. When the flow control system 38 is operated by means of the pump 32 and air pump 34 with valves 26a and 30a closed and valve 28a open, the standard solution 28 is saturated with dissolved oxygen, heated to about 30° C. by the heat exchanger 36 in the constant temperature bath 20, subsequently brought into contact with the other side 4b of the fixed-microorganism membrane 4 in the microorganism sensor 2, and then discharged from the system. According to the solute concentration of the standard solution 28, the activity of the nitrous acid-producing bacteria in the microorganism sensor 2 is lowered and the respiration amount for the nitrous acid-producing bacteria decreases, resulting in an increased sensor output current. Thus, a sensor output current corresponding to the solute concentration of the standard solution 28 is obtained and based on this, the microorganism sensor 2 is calibrated.

Quality examination of the test water 26 is conducted as follows. While the circulating system 54 is operated in the same manner as described above to circulate the buffer solution 18, the flow control system 38 is operated by means of the pump 32 and air pump 34 with valves 28a and 30a closed and valve 26a open. Upon the operation of the flow control system 38, test water 26 is saturated with dissolved oxygen, heated to about 30° C. by the heat exchanger 36 in the constant temperature bath 20, subsequently brought into contact with the other side 4b of the fixed-microorganism membrane 4 in the microorganism sensor 2, and then discharged from the system. After the completion of this examination, valve 26a is closed and valve 30a is opened, and cleaning water 30 is sent, by means of pump 32, to clean the system.

Figure 4:
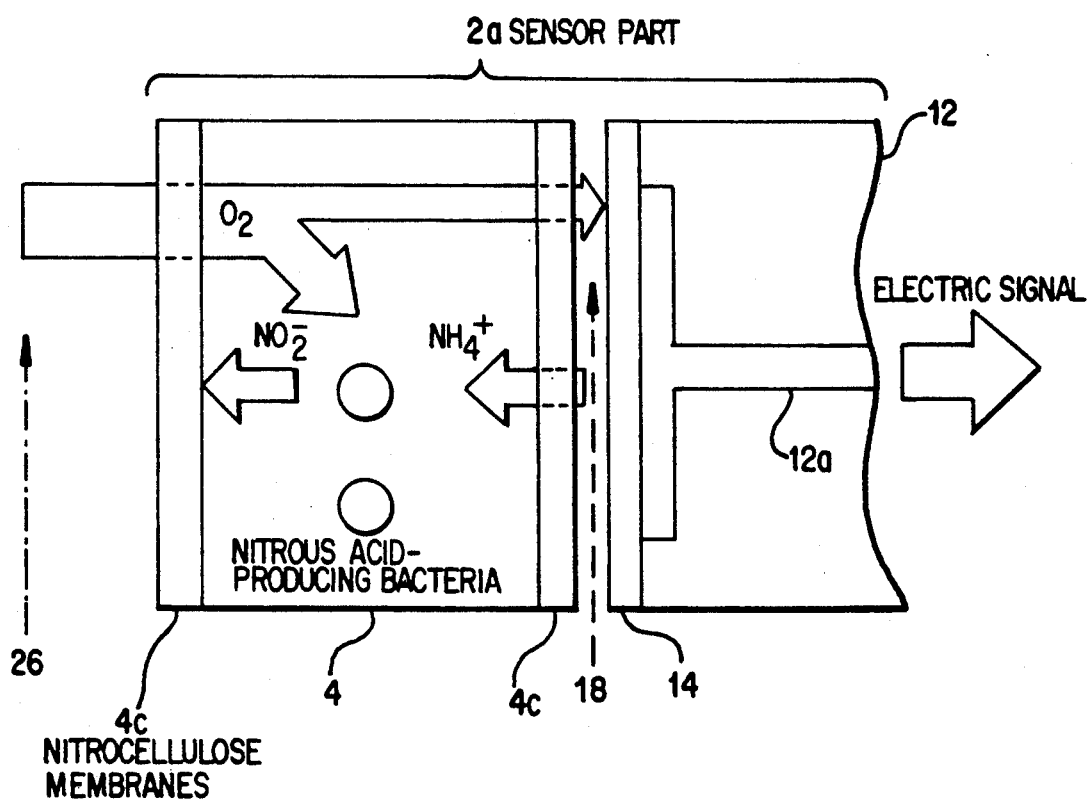
FIG. 4 is a diagrammatic view illustrating the principle of the operation of the microorganism sensor incorporated into the toxic substance-detecting device of this invention.

The principle on which the microorganism sensor 2 employing a nitrous acid-producing bacteria works is explained below. FIG. 4 is a diagrammatic view illustrating this principle. In FIG. 4, a sensor unit 2a includes a fixed-microorganism membrane 4 that can identify a toxic substance and a dissolved oxygen electrode 12. The fixed-microorganism membrane 4 has been prepared by inserting nitrous acid-producing bacteria, which selectively nitrify ammonia present in water into nitrous acid, between nitrocellulose membranes 4c having a thickness of 200 $\mu$m, and thereby fixing the bacteria to the membranes 4c. The flow of test water 26 is shown by an alternating long and short dashed line arrows and the flow of buffer solution 18 is shown by the dotted line arrows. The $NH_4^+$ present in the buffer solution 18 permeates through the nitrocellulose membranes 4c along with dissolved oxygen, upon which, the nitrous acid-producing bacteria causes a conversion of $NH_4^+ \longrightarrow NO_2^-$. Since the supply of a fixed concentration of $NH_4^+$ results in the consumption of dissolved oxygen in an amount equivalent to the $NH_4^+$ amount, a constant output level can be obtained by measuring the decreased amount of the dissolved oxygen by means of the dissolved oxygen electrode 12.

Figure 5:
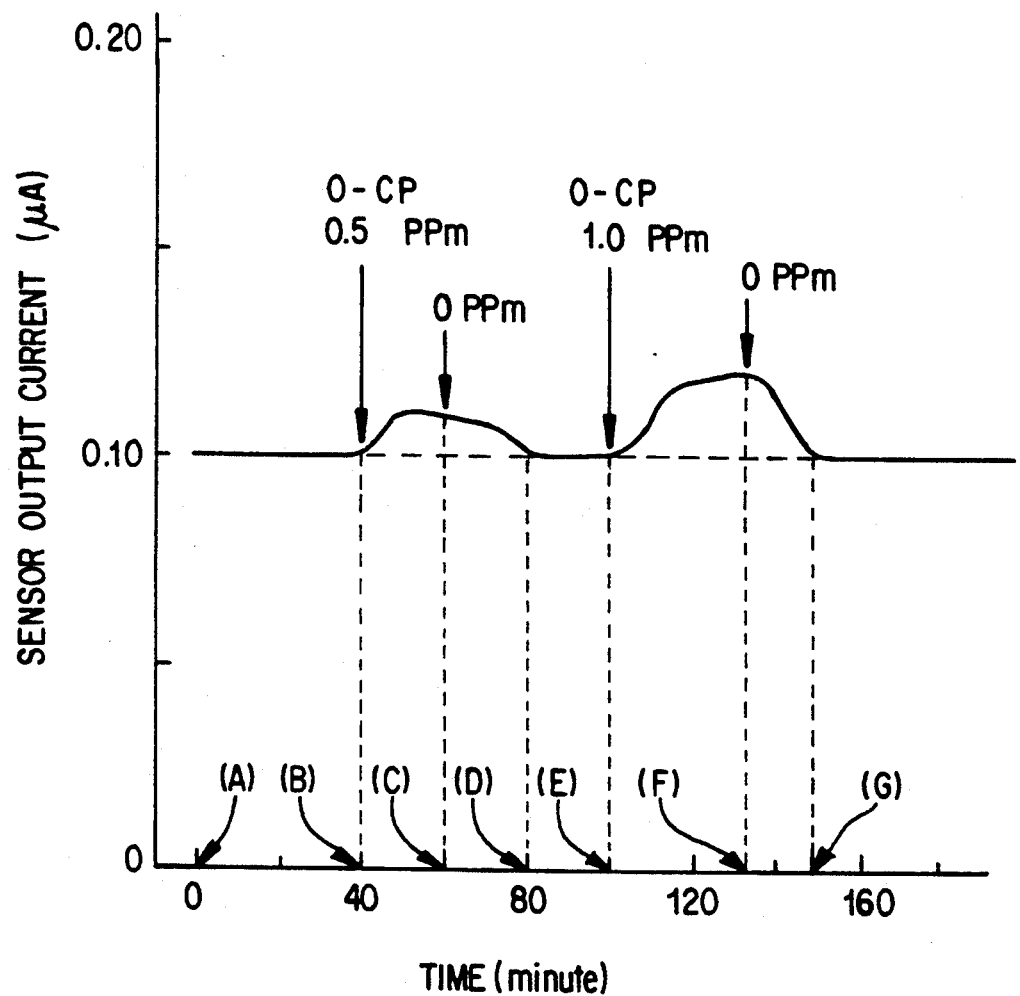
FIG. 5 is a graphic representation showing a time versus sensor output current curve obtained in a sample examination applying the toxic substance-detecting device of this invention.

FIG. 5 is a graph showing the results of a sample examination for the toxic substance-detecting device of this invention, and in which, time is the abscissa and sensor output current is the ordinate. In the case where no toxic substance has come into the test water 26 (O ppm), the sensor output current of the dissolved oxygen electrode 12 is a constant value corresponding to the concentration of the ammonia nitrogen incorporated in the buffer solution 18. This is due to nitrous acid-producing bacteria in the fixed-microorganism membrane 4 which nitrify ammonia nitrogen in the buffer solution 18 while consuming dissolved oxygen in the buffer solution 18. In FIG. 5, the above phenomenon corresponds to the sensor output current of 0.1 $\mu$A from (A) to (B), (D) to (E), and that extending from (G). After the nitrification, the resulting buffer solution 18 absorbs oxygen upon contact with air in an open atmosphere while being circulated. The dissolved oxygen is replenished to an amount equal to that consumed in the microorganism sensor 2 without additional exposure to air.

O-Chlorophenol (O-CP), which is one of the organic chlorine compounds regarded as toxic substances, is added to the test water 26 at concentrations of 0.5 ppm and 1.0 ppm and the test water is examined with the toxic substance-detecting device of this invention. The results are shown in FIG. 5. That is, when O-CP is added so that its concentration is changed to 0.5 ppm at time (B) and to O ppm at time (C), the activity of the nitrous acid-producing bacteria is lowered and the oxygen respiration amount for the bacteria is reduced depending on the O-CP concentration. As a result, the dissolved oxygen concentration in the test water 26 around the fixed-microorganism membrane 4 increases to a level higher than that of the dissolved oxygen concentration as measured at an O-CP concentration of O ppm, and the sensor output current increases as shown in FIG. 5. Because this response is reversible, the sensor output current returns to the original value, 0.1 $\mu$A, when the test water is replaced with one having a O-CP concentration of O ppm.

Figure 6:
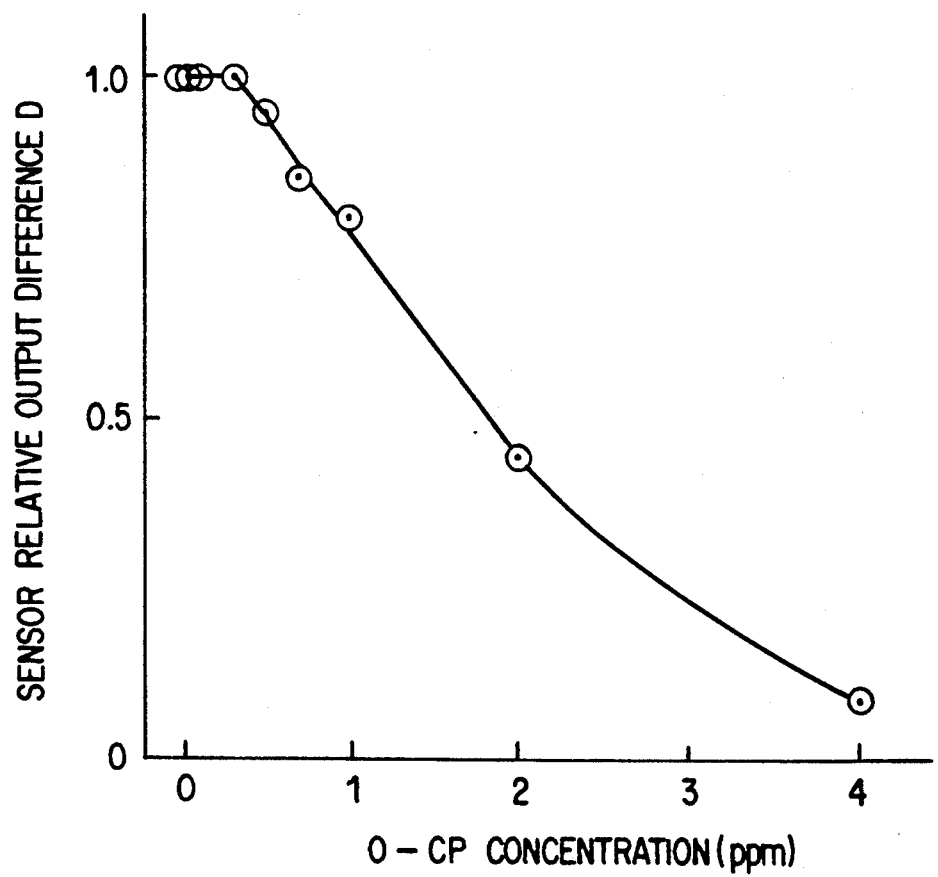
FIG. 6 is a graphic representation showing the relationship between O-CP (o-chlorophenol) concentration and sensor relative output difference.

FIG. 6 is a graph showing the relationship between 0-CP concentration and the sensor relative output difference as defined by the following equation (1), with the concentration being plotted as the abscissa and the sensor relative output difference as the ordinate.

Sensor relative output difference, $D = 1 - (A_c - A_O)/A_O$ (1)

$A_O$: sensor output current at an O-CP concentration of O ppm, $A_c$: sensor output current at an O-CP concentration of C ppm.

From the relationships shown in FIGS. 5 and 6, a sensor output current, depending on the O-CP concentration, can be obtained independent of the ammonia nitrogen contained in the test water 26 when the buffer solution 18 contains an excess of ammonia nitrogen. Therefore, it is possible to estimate the toxic substance concentration and the toxicity level.

Table 2 summarizes the minimum detectable concentrations and response times for various toxic substances. From Table 2, it can be understood that the toxic substances can be detected even when their concentrations are low, and that very quick detection is possible with the response times as short as about 10 to 15 minutes. The detectable concentration in Table 2 is defined as the concentration which causes the sensor output to decrease by 5% or more.

TABLE 2

| | Toxic Substance | Concentration (mg/l) | Detectable Concentration (mg/l) | Response Time (min) |
|---|---|---|---|---|
| Organic chlorine compound | o-chlorophenol | 0.034~6.80 | 0.12 | 10~15 |
| | trichloroethylene | 0.015~1.20 | 0.12 | 15~20 |
| | tetrachloroethylene | 0.019~0.37 | 0.08 | 15~20 |
| Health-affecting substance | cyanogen | 0.02~0.40 | 0.08 | 10~15 |
| | lead | 0.05~0.20 | 0.20 | 15~20 |
| | arsenic | 0.05~0.20 | 0.20 | 10~15 |

Although detailed explanations were given above with respect to the toxic substance-detecting device 1, a water quality-monitoring system employing this toxic substance-detecting device is necessary to conduct prompt water quality regulation of, for example, wastewaters discharged from factories.

Figure 7:
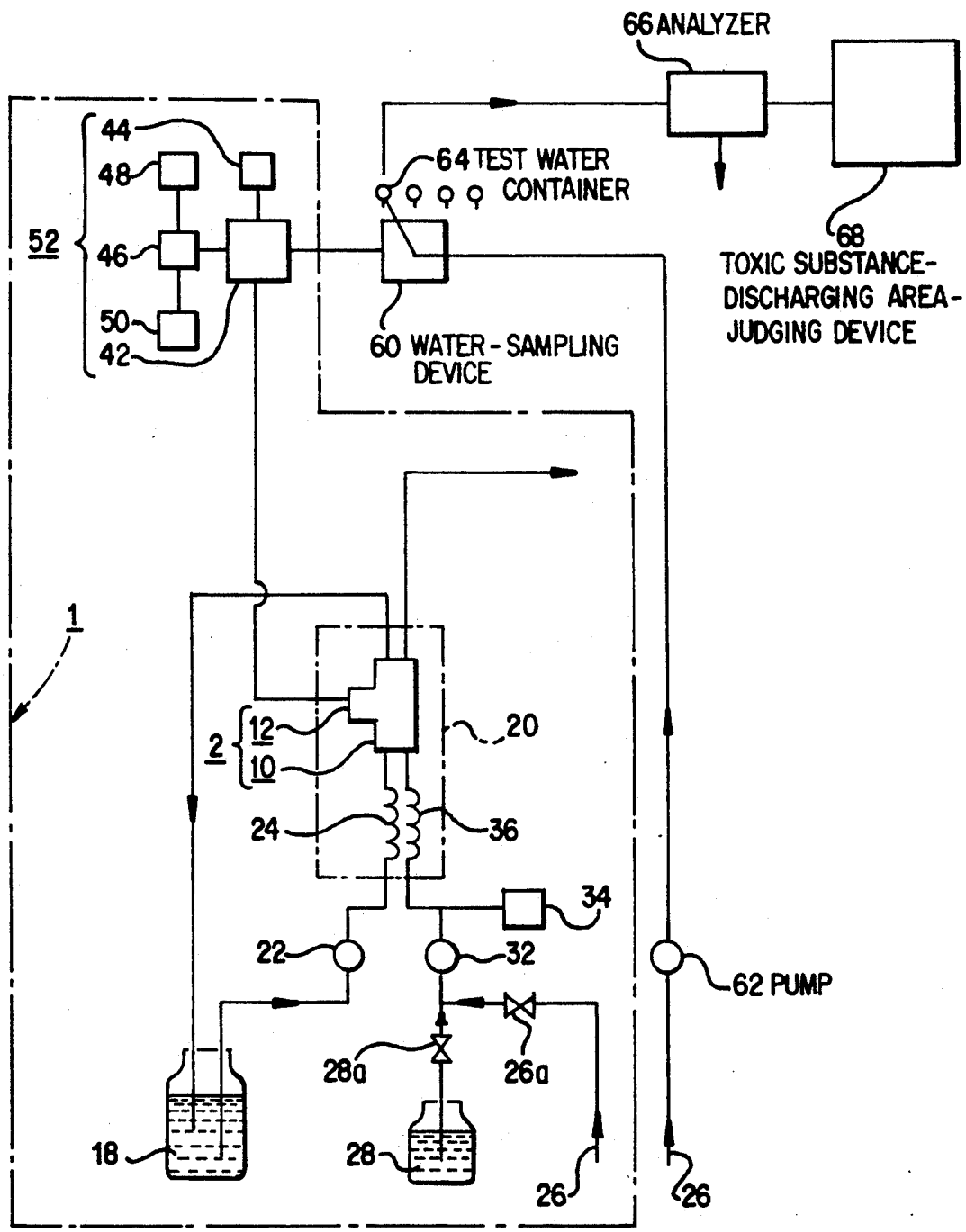
FIG. 7 is a diagrammatic view showing the construction of one embodiment of the water quality-monitoring system of this invention and the water channels in the system.

FIG. 7 is a diagrammatic view showing the construction of such a water quality-monitoring system and the water channels therein. In FIG. 7 and FIG. 2, like portions or parts are designated by like numerals. In FIG. 7, a water-sampling device 60 connected to the arithmetic and control circuit 52 of the toxic substance-detecting device 1, operates based on signals from the arithmetic and control circuit 52. That is, the water-sampling device 60 samples test water 26 by means of a pump 62 independently of the toxic substance-detecting device 1; subsequently places the water successively in a plurality of test water containers 64; and then sends the test water to an analyzer 66 where the test water 26 is analyzed to specify the toxic substance. A toxic substance-discharging area-judging device 68 connected to the analyzer 66 has been programmed beforehand to store information such as toxic substances with respect to facilities such as factories which have the possibility of discharging wastewaters contaminated by toxic substances and which are located in the basin of the rivers whose waters are to be monitored. Results of the analysis by the analyzer 66 are sent to the toxic substance-discharging area-judging device 68, upon which the judging device 68 estimates the area or the facilities that may be the source of the toxic substance and displays them on a screen. By utilizing such a water quality-monitoring system in treatment processes for tap water or sewage, it becomes possible to take proper measures against toxic substances before contaminated wastewaters flow into the water-treating processes.

As described above, in the case where a toxic substance has come into the test water to be examined, the toxic substance-detecting device of the present invention can rapidly detect the presence of the toxic substance in a short period of time with high sensitivity. This is possible through the use of (1) a microorganism sensor based on a combination of a fixed-microorganism membrane on which a nitrous acid-producing bacteria, an autotrophic bacteria sensitive to toxic substances, has been fixed; (2) a dissolved oxygen electrode; and (3) a construction including: a circulating system which sends a buffer solution to one side of the fixed-microorganism membrane, a flow control system which selectively sends test water or a standard solution to the other side of the fixed-microorganism membrane and an arithmetic and control circuit which processes outputs from the microorganism sensor and controls the operation. That is, by the presence of the toxic substance that has come into the test water, the ammonia-oxidizing activity of the nitrous acid-producing bacteria in the microorganism sensor is lowered and, as a result, the microorganism sensor output increases, indicating the presence of the toxic substance. In the case of sewage treatment, for example, the detecting device of this invention is effective in detecting many kinds of toxic organic chlorine compounds in the test water that lower the activity of the activated-sludge microorganisms or annihilate the microorganisms. The detecting device of this invention has a further advantage that its maintenance is far easier than that of the conventional toxic substance-detecting technique for tap water which utilizes a technique based on maintaining fish.

The water quality-monitoring system utilizing the toxic substance-detecting device can conduct continuous monitoring and detect toxic substances in a short period of time. In addition, the system can finally specify the toxic substance and reveal the area from which the toxic substance has been discharged. Therefore, the water quality-monitoring system of this invention is also effective in regulating, at early stages, the quality of wastewaters discharged from such places as factories or in taking proper measures against toxic substances beforehand.

While the invention has been described in detail and with reference to specific embodiments thereof, it will be apparent to one skilled in the art that various changes and modifications can be made therein without departing from the spirit and scope thereof.

What is claimed is:

1. A toxic substance-detecting device comprising:
a microorganism sensor comprising a flow cell including a fixed-microorganism membrane having a first side and a second side, said sides being separated by the membrane thickness and a dissolved oxygen electrode, said dissolved oxygen electrode being in contact with said first side of said fixed-microorganism membrane;
circulating means connected to said microorganism sensor through a first heat exchanger for circulating a buffer solution from a source of buffer solution and sending said buffer solution to said first side of said fixed-microorganism membrane;
flow control means connected to said microorganism sensor through a second heat exchanger for selectively supplying, at any one time, one of the following solutions to said second side of said fixed-microorganism membrane from respective sources: (1) water to be examined, (2) a standard solution, and (3) cleaning water; and
an arithmetic and control circuit arranged for receiving output signals from said microorganism sensor through a conducting means and processing said output signals to control operation of components of said toxic substance-detecting device.

2. A toxic substance-detecting device according to claim 1, wherein nitrous acid-producing bacteria are fixed on said fixed-microorganism membrane, and wherein two flow channels are in contact with said first and second sides of said fixed-microorganism membrane, respectively.

3. A toxic substance-detecting device according to claim 1, wherein said dissolved oxygen electrode is in contact with said first side of said fixed-microorganism membrane through a gas-permeable membrane to measure the amount of dissolved oxygen within said fixed-microorganism membrane.

4. A toxic substance-detecting device according to claim 1, wherein said buffer solution used in said device contains, at a predetermined concentration, an ammonia nitrogen, said ammonia nitrogen providing a substrate for nitrous acid-producing bacteria in said fixed-microorganism membrane.

5. A toxic substance-detecting device according to claim 1, wherein said flow control means comprises means for saturating said water to be examined and said standard solution with dissolved oxygen prior to being sent to said second side of said fixed-microorganism membrane.

6. A toxic substance-detecting device according to claim 1, wherein said fixed-microorganism membrane is a nitrocellulose membrane.

7. A toxic substance-detecting device according to claim 1, wherein said first heat exchanger heats said buffer solution to a first predetermined temperature and said second heat exchanger heats one of said water to be examined and said standard solution to a second predetermined temperature.

8. A toxic substance-detecting device according to claim 7, wherein said first and second predetermined temperatures are approximately 30° C.

9. A toxic substance-detecting device according to claim 1, wherein said standard solution is used to calibrate said microorganism sensor and said cleaning water is used to clean said second side of said fixed-microorganism membrane.

10. A toxic substance-detecting device according to claim 1, wherein said dissolved oxygen electrode comprises a platinum cathode that is in contact with said fixed-microorganism membrane through a gas-permeable membrane.

11. A toxic substance-detecting device according to claim 1, wherein said conducting means comprises an electrical wire.

12. A water quality-monitoring system comprising:
a microorganism sensor comprising a flow cell including a fixed-microorganism membrane having a first side and a second side, said sides being separated by the membrane thickness and a dissolved oxygen electrode, said dissolved oxygen electrode being in contact with said first side of said fixed microorganism membrane;
circulating means connected to said microorganism sensor through a first heat exchanger for circulating a buffer solution from a source of buffer solution and sending said buffer solution to said first side of said fixed-microorganism membrane;
flow control means connected to said microorganism sensor through a second heat exchanger for selectively supplying, at any one time, one of the following three solutions to said second side of said fixed-microorganism membrane from respective sources: (1) water to be examined, (2) a standard solution, and (3) cleaning water;
an arithmetic and control circuit arranged for receiving output signals from said microorganism sensor through a first conducting means and processing said output signals to control operation of components of water quality-monitoring system;
water-sampling means for receiving output signals from said arithmetic and control unit through a second conducting means and for continuously taking samples of said water to be examined;
chemical analyzing means for receiving said water samples from said water sampling device and for quantitatively analyzing said received water samples to produce analyzed signals; and
toxic substance-discharging area-judging means for receiving analyzed signals from said chemical analyzer and estimating a source of a toxic substance.

13. A water quality-monitoring system according to claim 12, wherein nitrous acid-producing bacteria are fixed on said fixed-microorganism membrane and two flow channels are in contact with said first and second sides of said fixed-microorganism membrane, respectively.

14. A water quality-monitoring system according to claim 12, wherein said dissolved oxygen electrode is in contact with said second side of said fixed-microorganism membrane through a gas-permeable membrane to measure the amount of dissolved oxygen within said fixed-microorganism membrane.

15. A water quality-monitoring system according to claim 12, wherein said buffer solution used in said device contains, at a predetermined concentration, an ammonia nitrogen, said ammonia nitrogen providing a substrate for nitrous acid-producing bacteria in said fixed-microorganism membrane.

16. A water quality-monitoring system according to claim 12, wherein said flow control means comprises means for saturating said water to be examined and said standard solution with dissolved oxygen prior to being sent to said second side of said fixed-microorganism membrane.

17. A toxic substance-detecting device according to claim 12, wherein said fixed-microorganism membrane is a nitrocellulose membrane.

18. A toxic substance-detecting device according to claim 12, wherein said first heat exchanger heats said buffer solution to a first predetermined temperature and said second heat exchanger heats one of said water to be examined and said standard solution to a second predetermined temperature.

19. A toxic substance-detecting device according to claim 18, wherein said first and second predetermined temperatures are approximately 30° C.

20. A toxic substance-detecting device according to claim 12, wherein said standard solution is used to calibrate said microorganism sensor and said cleaning water is used to clean said second side of said fixed-microorganism membrane.

21. A toxic substance-detecting device according to claim 12, wherein said dissolved oxygen electrode comprises a platinum cathode that is in contact with said fixed-microorganism membrane through a gas-permeable membrane.

22. A toxic substance-detecting device according to claim 12, wherein said conducting means comprises an electrical wire.

* * * * *

UNITED STATES PATENT AND TRADEMARK OFFICE
CERTIFICATE OF CORRECTION

PATENT NO. : 5,160,604
DATED : November 03, 1992
INVENTOR(S) : Eiichi Nakamura et al.

It is certified that error appears in the above-identified patent and that said Letters Patent is hereby corrected as shown below:

On the Title page, Abstract, Line 10 change "membranne" to --membrane--.

Claim 1, column 10, line 17, before "solutions" insert --three--.

Claim 12, column 11, line 31, before "water" insert --said--.

Claim 12, column 11, line 37, change "water sampling" to --water-sampling--.

Signed and Sealed this

Fourth Day of January, 1994

Attest:

BRUCE LEHMAN

Attesting Officer

Commissioner of Patents and Trademarks